US012216990B2

(12) United States Patent
Martinez et al.

(10) Patent No.: US 12,216,990 B2
(45) Date of Patent: Feb. 4, 2025

(54) VOICE ACTIVATED CLINICAL REPORTING SYSTEMS AND METHODS THEREOF

(71) Applicant: Clickview Corporation, San Francisco, CA (US)

(72) Inventors: David A. Martinez, San Francisco, CA (US); David K. Martinez, San Francisco, CA (US)

(73) Assignee: ClickView Corporation, San Francisco, CA (US)

( * ) Notice: Subject to any disclaimer, the term of this patent is extended or adjusted under 35 U.S.C. 154(b) by 336 days.

(21) Appl. No.: 17/521,375

(22) Filed: Nov. 8, 2021

(65) Prior Publication Data

US 2022/0147703 A1 May 12, 2022

Related U.S. Application Data

(60) Provisional application No. 63/110,896, filed on Nov. 6, 2020.

(51) Int. Cl.
| | |
|---|---|
| *G06F 40/18* | (2020.01) |
| *G06F 40/186* | (2020.01) |
| *G10L 15/18* | (2013.01) |
| *G10L 15/22* | (2006.01) |
| *G16H 15/00* | (2018.01) |
| *G10L 15/08* | (2006.01) |

(52) U.S. Cl.
CPC ............ *G06F 40/186* (2020.01); *G10L 15/18* (2013.01); *G10L 15/22* (2013.01); *G16H 15/00* (2018.01); *G10L 2015/088* (2013.01)

(58) Field of Classification Search
CPC ..... G06F 40/186; G06F 40/205; G16H 15/00; G10L 15/26; G10L 15/1815; G10L 15/1822

See application file for complete search history.

(56) References Cited

U.S. PATENT DOCUMENTS

| | | | | |
|---|---|---|---|---|
| 2005/0228815 | A1* | 10/2005 | Carus | G16H 10/60 707/999.102 |
| 2011/0301943 | A1* | 12/2011 | Patch | G06F 3/167 704/9 |
| 2018/0240538 | A1* | 8/2018 | Koll | G16H 10/60 |

* cited by examiner

*Primary Examiner* — Mark Villena
(74) *Attorney, Agent, or Firm* — Troutman Pepper Hamilton Sanders LLP

(57) ABSTRACT

A method for automatically generating clinical structured reports based on templates using voice recognition, the method implemented by a computing device and includes applying a natural language processing algorithm to a captured voice input from a client to identify one or more keywords or phrases. At least one of a plurality of clinical structured report templates are identified based on the identified one or more keywords or phrases correlated to medical examination data points associated with each of the templates. A clinical structured report is automatically prepared based on the identified clinical structured report templates without a non-voice input and without an explicit separate voice command directed to manage a report generation operation. The clinical structured report includes modifications to the clinical structured report template based on the identified one or more keywords or phrases. The clinical structured report is provided to the client.

36 Claims, 10 Drawing Sheets

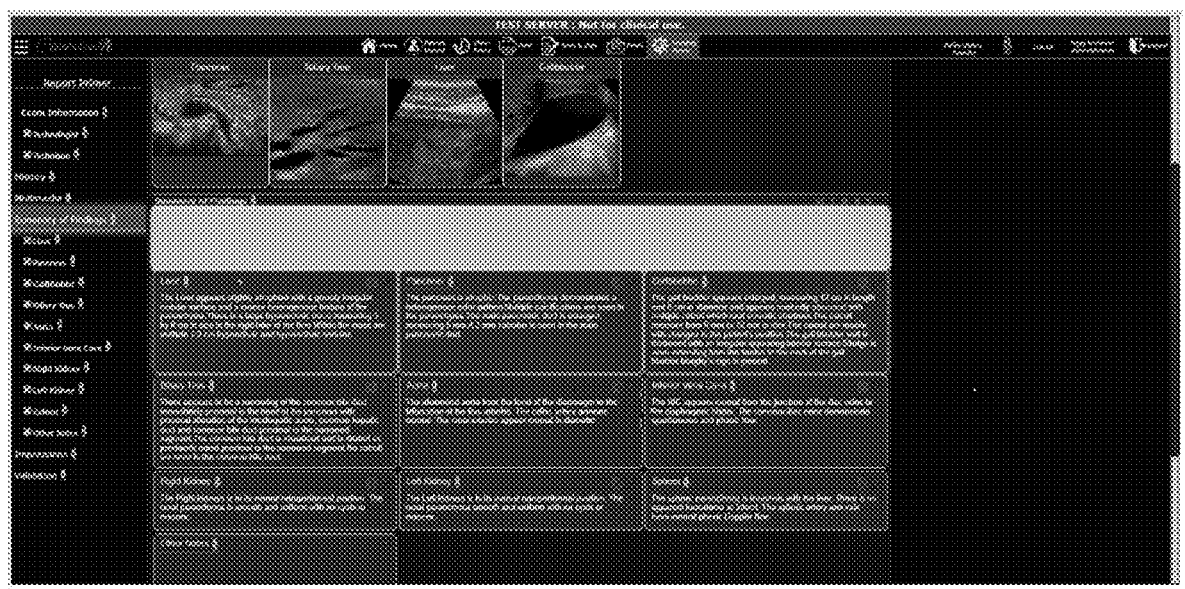
FIG. 5: Sample Screen Capture of User Display

| | System Navigation Bar (Fixed) | |
|---|---|---|
| Report Primer<br><br>(Visible/Hidden Optional) | Current Template Navigation Bar (Exam Specific and Configurable) | Smart Engine<br><br>(Hidden) |
| The Report Primer is the core voice navigation method for report generation and is automatically configured from the system database with key words for specific exam type and anatomical content.<br><br>• Exam Information<br>• History<br>• Multimedia<br>• Summary of Findings<br>   o Section 1 (i.e., Liver)<br>      Sub-section A (i.e., Right Lobe)<br>   o Section 2, Etc.<br>   o Section 3, Etc.<br>• Impressions<br>• Recommendation<br>• Validation<br>• Addendums<br>• Exam Status | < Exam Type> for < F.Name, L Name><br><br>Exam Technique Information<br><br>Draft Report Notification Banner<br><br>Patient History<br><br>Multimedia: Images, Illustrations, Charts, Video Clips<br><br>Optional Data Table<br><br>Text Content Summary of Findings Specific to Exam Type Including Sub-Sections<br><br>Diagnostic Impressions<br><br>Optional Recommendation<br><br>Examiner's Sign Off Validation<br><br>Addendums<br><br>Exam Status: Draft or Final | Algorithm Management System for Voice Processing for Specific Report Configuration, Type of Command: Raw Text, Macro, Navigation, and Input Execution<br><br>Exam Specific Content Database<br><br>(Hidden<br><br>Exam Specific Report Configuration, Anatomical Content & Macro Library |

FIG. 6: Schematic Diagram of the User Worksheet Interface

FIG. 10: The Report Primer

| Current Active Worksheet Template |
|---|
| (Exam Specific) |
|  |
| Patient Demographics |
| Exam Type |
| Exam Technique Information |
| Draft Report Notification Banner |
|  |
| Patient History |
| Multimedia: Images, Illustrations, Charts, Video Clips |
| Optional Data Table |
| Findings and Summary of Findings<br><br>(Content Specific to Exam Type Including Sub-Sections) |
| Diagnostic Impressions |
| Optional Recommendation |
|  |
| Examiner's Sign Off Validation |
|  |
| Addendums |
| Exam Status: Draft or Final |

FIG. 11: Current Active Worksheet Template

FIG. 12: The Smart Findings Engine Text Input Box 'The liver appears slightly atrophied' is automatically placed in the Liver text box based on detection of the key word 'liver'.
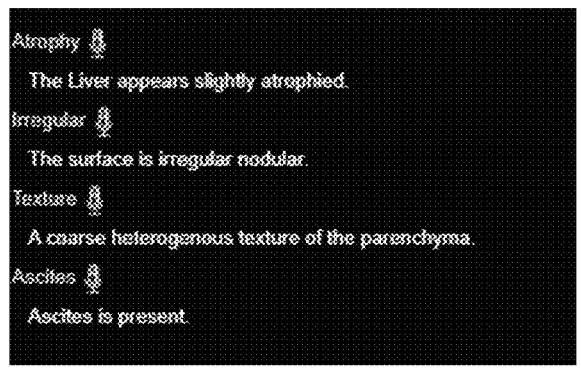
FIG. 13: User Defined Macro Keywords
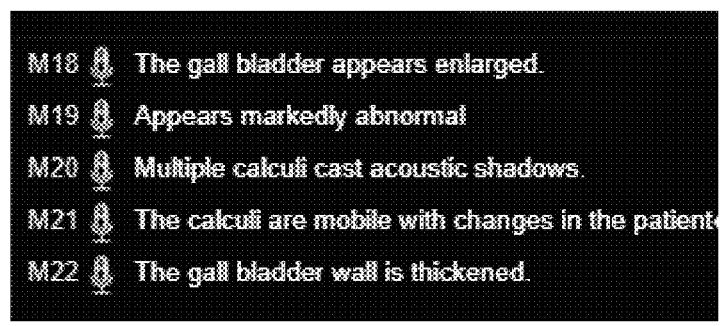
FIG. 14: System Defined Macro Key Words

VOICE ACTIVATED CLINICAL REPORTING SYSTEMS AND METHODS THEREOF

This application claims the benefit of U.S. Provisional Patent Application Ser. No. 63/110,896, filed Nov. 6, 2020, which is hereby incorporated by reference in its entirety.

FIELD

This technology relates to methods and systems for creating a medical examination structured report with automated integrated voice activated algorithms that replace mouse, keyboard, and microphone and 'tab+command' systems as input devices.

BACKGROUND

Currently in the healthcare industry, technicians, and physicians summarize a patient's visit for a clinical evaluation or procedure as a report detailing and evaluating all information available at the time of the visit. This clinical evaluation report is commonly generated by conventional reporting systems in which the user is required to utilize a variety of computer mouse and keyboard setups as input devices to select, insert and accept text, macro phrases, and other report elements in generation of the report.

Voice to text speech recognition systems provide the ability to enter text statements into report fields using a microphone and 'tab+command' systems to navigate to the proper field for text entry. In these systems the user 'tabs' a microphone manually to place a cursor in the correct data entry field then speaks a command to complete execution. If the desired data entry insertion field is not displayed on the user's current screen, the user will be required to scroll up or down the screen field of view in order to select the correct point of insertion.

Unfortunately, with daily medical practices, mouse, keyboard, microphone, and 'tab+command' systems are cumbersome tools with which to enter clinical information and data. In particular, they are clumsy and inefficient for navigation, unnecessarily prolong report generation process, decrease user productivity, and distract the user from the critical task of closely evaluating the clinical and procedure findings in order to make an accurate diagnosis.

In currently available structured reporting systems, the entire length and width of the draft report template into which information is to be entered is often several times greater than the computer screen display ViewPort (one screen height/width unit). Further, the structured report template is often formatted in a simple serial manner for data entry. The structured reporting template often starts at the top of a template and scrolls from top to bottom to enter data in a serial manner in order to complete the report. Alternately, the user's system may be formatted in a sequence of data entry pages displayed in a left to right serial manner analogous to vertical scrolling systems.

In either scrolling template or the alternate multiple page structured report template design, the user is dependent on the physical process of multiple keyboard, mouse, or 'tab' clicks for microphone devices to navigate the structured report template in order to select the correct template field for the appropriate data or text insertion.

However, in everyday use, the process of actually completing a draft report in a structured report template is dynamic, and the user is constantly evaluating the aggregation of new information as the report is built and will frequently need to edit prior or subsequent text or macro entries. This live editing during the draft report preparation process requires the user's workflow to dynamically move to different sections of the report template in a random manner that is clearly out of sequence with the standard rigid underlying report template serial workflow.

For example, once data and information entry into a draft report template in preparation is completed by the user, a final review may often require that the user move to multiple sections of the report for further corrections, constantly editing by the addition or deletion of inserted information in order to assure an accurate final report. This will typically require a cumbersome series of keyboard, mouse, and microphone and 'tab+command' system clicks and scrolls that interrupt the users mental diagnostic process and physical workflow, and is time consuming, slowing the report generation process while increasing the well documented frequency of errors in data entry, critically impacting report accuracy, and the quality of patient care.

In current reporting systems, content, such as text, macro phrases, and numerical values, inserted into a structured report template by the user must be placed into the correct topic (i.e. Liver, Spleen, Pancreas, etc.), section and subsection, and in the correct order of the report fields manually with keyboard, mouse, or microphone and 'tab+command' system functions.

For example, ideally, a spoken sentence like, "The Liver is severely atrophied. The right lobe measures eight centimeters in width and four centimeters in depth." should automatically be recognized as a commentary on the Liver, not part of a commentary about the Spleen, Pancreas, or even the Eyes. Similarly, the measurements describing the size of the right lobe should appear in the correct section of the right lobe of the liver and in the correct order without requiring the user to use the keyboard, mouse or microphone tab function. However, as discussed above conventional reporting systems have been unable to address these long standing deficiencies.

SUMMARY

A method for automatically generating clinical structured reports based on clinical structured report templates using voice recognition, the method implemented by one or more report management computing devices and includes applying a natural language processing algorithm to a captured voice input from a client to identify one or more keywords or phrases. At least one of a plurality of clinical structured report templates are identified based on the identified one or more keywords or phrases correlated to medical examination data points associated with each of the clinical structured report templates. A clinical structured report is automatically prepared based on the identified one of the clinical structured report templates without a non-voice input and without an explicit separate voice command directed to manage a report generation operation. The clinical structured report includes modifications to the clinical structured report template based on the identified one or more keywords or phrases. The prepared clinical structured report is provided to the client.

A voice activated clinical structured reporting device, comprising memory comprising programmed instructions stored thereon and one or more processors configured to execute the stored programmed instructions to apply a natural language processing algorithm to a captured voice input from a client to identify one or more keywords or phrases. At least one of a plurality of clinical structured report templates are identified based on the identified one or more keywords or phrases correlated to medical examination data points associated with each of the clinical structured report templates. A clinical structured report is automatically prepared based on the identified one of the clinical structured report templates without a non-voice input and without an explicit separate voice command directed to manage a report generation operation. The clinical structured report includes modifications to the clinical structured report template based on the identified one or more keywords or phrases. The prepared clinical structured report is provided to the client.

A non-transitory machine readable medium having stored thereon instructions for voice activate clinical structured reporting comprising executable code that, when executed by one or more processors, causes the processors to apply a natural language processing algorithm to a captured voice input from a client to identify one or more keywords or phrases. At least one of a plurality of clinical structured report templates are identified based on the identified one or more keywords or phrases correlated to medical examination data points associated with each of the clinical structured report templates. A clinical structured report is automatically prepared based on the identified one of the clinical structured report templates without a non-voice input and without an explicit separate voice command directed to manage a report generation operation. The clinical structured report includes modifications to the clinical structured report template based on the identified one or more keywords or phrases. The prepared clinical structured report is provided to the client.

This technology provides a number of advantages including providing an intelligent automated voice activated clinical reporting system that eliminates the need for separate mouse, keyboard, and microphone and 'tab+command' systems or without additional separate explicit voice operation commands as input mechanisms to accurately generate clinical structured reports. Examples of this technology address at least three major issues characteristic of contemporary structured reporting template systems as discussed above including: (1) hardware limitations; (2) navigation limitations; and (3) lack of intelligence of the system. These prior issues have historically affected the accuracy, ease of report preparation, speed of generation of a clinical report, and importantly a user's productivity which examples of the claimed technology are able to overcome. By way of example, this technology manages a "smart engine" of intelligent algorithms which detect keywords and phrases in natural language speech as inputs which automatically create instructions for executable processes to create examination specific report templates, select and manipulate multimedia report elements, and enable automatic and dynamic template and system navigation processes, without additional explicit voice commands, for the generation of a completed clinical structured patient report. Examples of this technology utilize voice activated executable algorithms managed by a smart engine to navigate the active focus within and/or external to the structured report template to select, insert, accept, and manipulate text and multimedia report elements necessary for report generation. Accordingly, examples of this technology have adapted integrated speech recognition without additional and separate explicit voice commands as the sole input component to manage an integrated system of intelligent algorithms responsive to automatically create instructions for executable processes to generate a completed clinical structured report. As a result, with this technology, a user is able to focus on critical diagnostic implications of the findings of the clinical or procedure at hand and is freed from the distraction and clumsiness of separate mouse, keyboard, and microphone and 'tab+command' systems as input mechanisms or even the requirement for additional explicit voice commands.

BRIED DESCRITION OF THE DRAWINGS

FIG. 5 is a screenshot of an example of a user display of an exemplary clinical structured report being generated.

FIG. 6 is a diagram of an example of a user worksheet interface.

FIG. 10 is a screenshot of an example of a display of a report primer for voice active clinical structured reporting.

FIG. 11 is a diagram of an example of a current active worksheet template.

FIG. 12 is a screenshot of an example of a smart findings display of a report primer for voice active clinical structured reporting.

FIG. 13 is a screenshot of an example of user defined macro operations for voice active clinical structured reporting.

FIG. 14 is a screenshot of an example of system defined macro operations for voice active clinical structured reporting.

DETAILED DESCRIPTION

Figure 1:
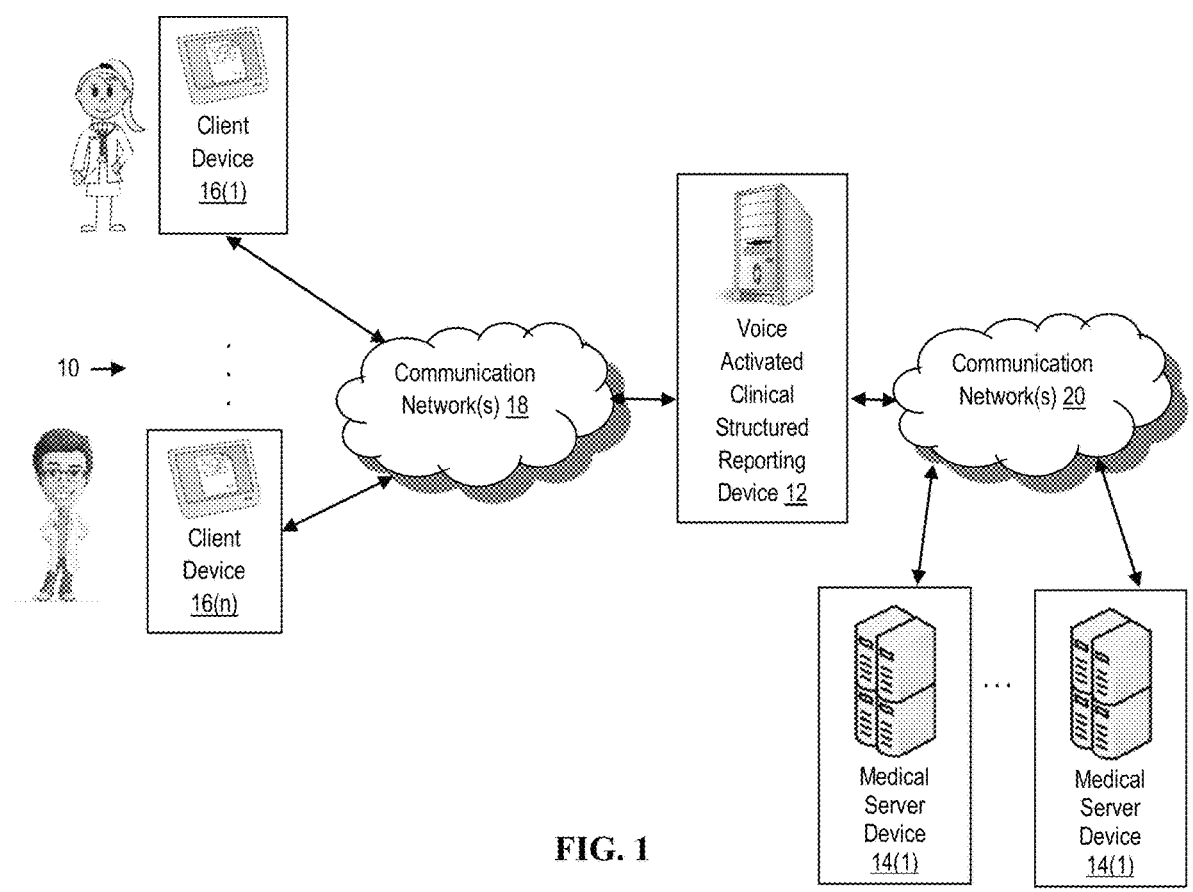
FIG. 1 is a diagram of an exemplary environment with an example of a voice active clinical structured reporting device.
Figure 2:
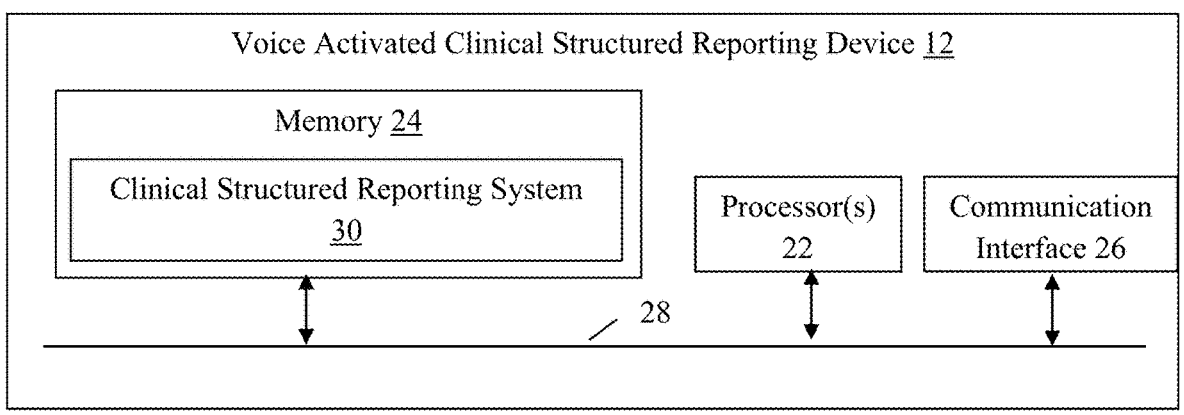
FIG. 2 is a block diagram of the example of the voice active clinical structured reporting device shown in FIG. 1.

An exemplary network environment 10 with an example of an intelligent voice activated clinical structured reporting device 12 is illustrated in FIGS. 1-2. The exemplary environment 10 includes the voice activated clinical structured reporting device 12, a plurality of medical server devices 14(1)-14(n) and a plurality of client devices 16(1)-16(n) coupled together by communication networks 18 and 20, although the exemplary environment could include other types and/or numbers of other systems, devices, components, and/or other elements in other configurations. This technology provides a number of advantages including providing an intelligent automated voice activated clinical reporting system that eliminates the need for separate mouse, keyboard, and microphone and 'tab+command' systems or without additional separate explicit voice commands as input mechanisms to accurately generate clinical structured reports. As illustrated by way of example herein, this technology advantageously relies solely on voice recognition without separate explicit voice commands, which eliminates the need and inconvenience of using other input mechanisms.

For the examples illustrated and described herein for illustrative purposes only and not limited to the description below, a report (also referred to as a clinical structured report in these examples, is a logical, structured representation of a collection of information regarding a patient's clinical visit. A worksheet in these examples is the graphical user interface used to insert, edit, prepare and perform quality assurance on the text, numerical and multimedia information to be used in the generation of the final report as illustrated by way of example in FIG. 6. A band in these examples is one segment of the clinical structured report. A report may comprise for example: multiple bands; multimedia; and a summary of finding. A section in these examples is a sub-segment of a band. A band may contain one or more sections, such as Liver, Spleen, Right Kidney, etc. by way of example. A state of a section in these examples is the current view of a section and a section may have two or more states, such as view or edit, but may exist only in one state at any time. Raw text in these examples is defined as text generated from raw natural language processing of voice input that was spoken directly into and captured by a microphone or other audio capture input mechanism which is converted by a speech recognition application executing at the one of the client devices 16(1)-16(n) to the raw text with no additional word processing done on this input. As illustrated and described by way of the examples herein, the voice activated clinical structured reporting device 12 manages and manipulates text for the purposes of generation of a structured report including by way of example template identification, template formatting, internal and external content processing and retrieval as needed, and navigation by way of example. A macro keyword in these examples is a word or words that fires functionality or executes an instruction to for example insert a macro phases into a text box. A navigation keyword in these examples is a word that for example navigates the active focus of the structured reporting worksheet within a template to that section of the worksheet, or to a system page external to the current patient report template without the need for a separate explicit voice command for the navigation operation. A functional keyword in these examples defines a word that triggers a change in the state of a section, such as edit or show by way of example.

Referring more specifically to FIGS. 1-2, the voice activated clinical structured reporting device 12 in this example includes processor(s) 22, a memory 24, and/or a communication interface 26, which are coupled together by a bus 28 or other communication link, although the voice activated clinical structured reporting device 12 can include other types and/or numbers of elements in other configurations. The processor(s) 22 of the voice activated clinical structured reporting device 12 may execute programmed instructions stored in the memory 24 for the any number of the functions described and illustrated herein. The processor(s) 22 of the voice activated clinical structured reporting device 12 may include one or more CPUs or general purpose processors with one or more processing cores, for example, although other types of processor(s) can also be used.

The memory 24 of the voice activated clinical structured reporting device 12 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s) 22, can be used for the memory 24.

Accordingly, the memory 24 of the voice activated clinical structured reporting device 12 can store application(s) that can include executable instructions that, when executed by the processor(s) 22, cause the voice activated clinical structured reporting device 12 to perform actions, such as described and illustrated below with reference to FIGS. 3-14. The application(s) can be implemented as modules or components of other application(s). Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the voice activated clinical structured reporting device 12 itself, may be located in virtual server(s) running in a cloud-based computing environment rather than being tied to one or more specific physical network computing devices. Also, the application(s) may be running in one or more virtual machines (VMs) executing on the voice activated clinical structured reporting device 12. Additionally, in one or more embodiments of this technology, virtual machine(s) running on the voice activated clinical structured reporting device 12 may be managed or supervised by a hypervisor.

In this particular example, the memory 24 of the voice activated clinical structured reporting device 12 includes a clinical structured reporting system 30 that serves as a smart engine for the voice activated clinical structured reporting device 12, although the memory 24 can include other policies, modules, databases, or applications, for example. The clinical structured reporting system 30 in this example is configured with programmed instructions, modules, and/ or other data to for example manage algorithms associated with the workflow of the voice activated clinical structured reporting device 12, create executable instructions for one or more of the processes described herein, triage voice commands, and format the report primer as described below in FIGS. 3-14, for example. The clinical structured reporting system 30, as shown in greater detail in the example in FIG. 3, that is configured to manage generation of a clinical structured report by the voice activated clinical structured reporting device 12.

Figure 3:
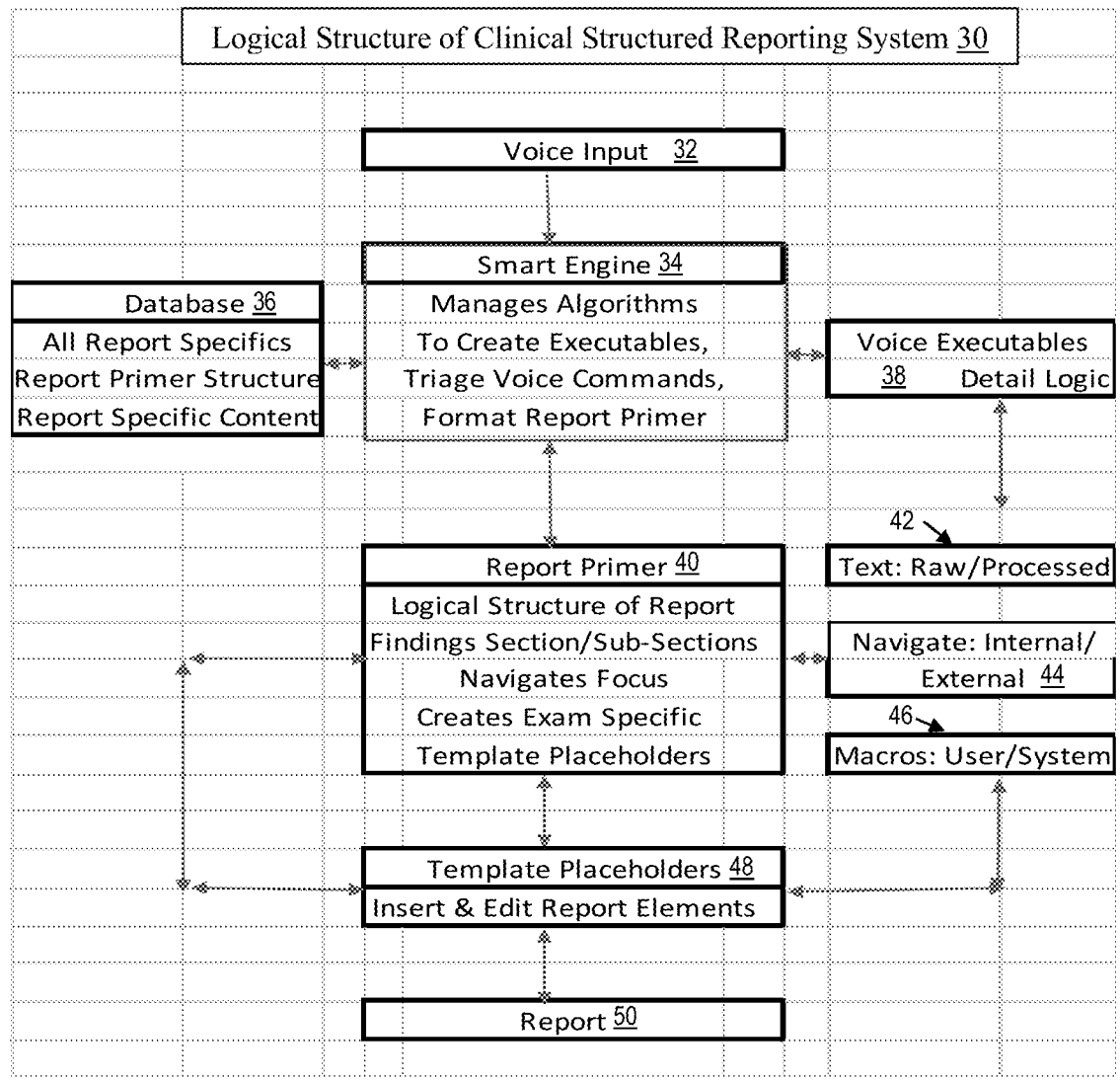
FIG. 3 is a logical structure diagram of an example of the clinical structured reporting system shown in FIG. 2.
Figure 4:
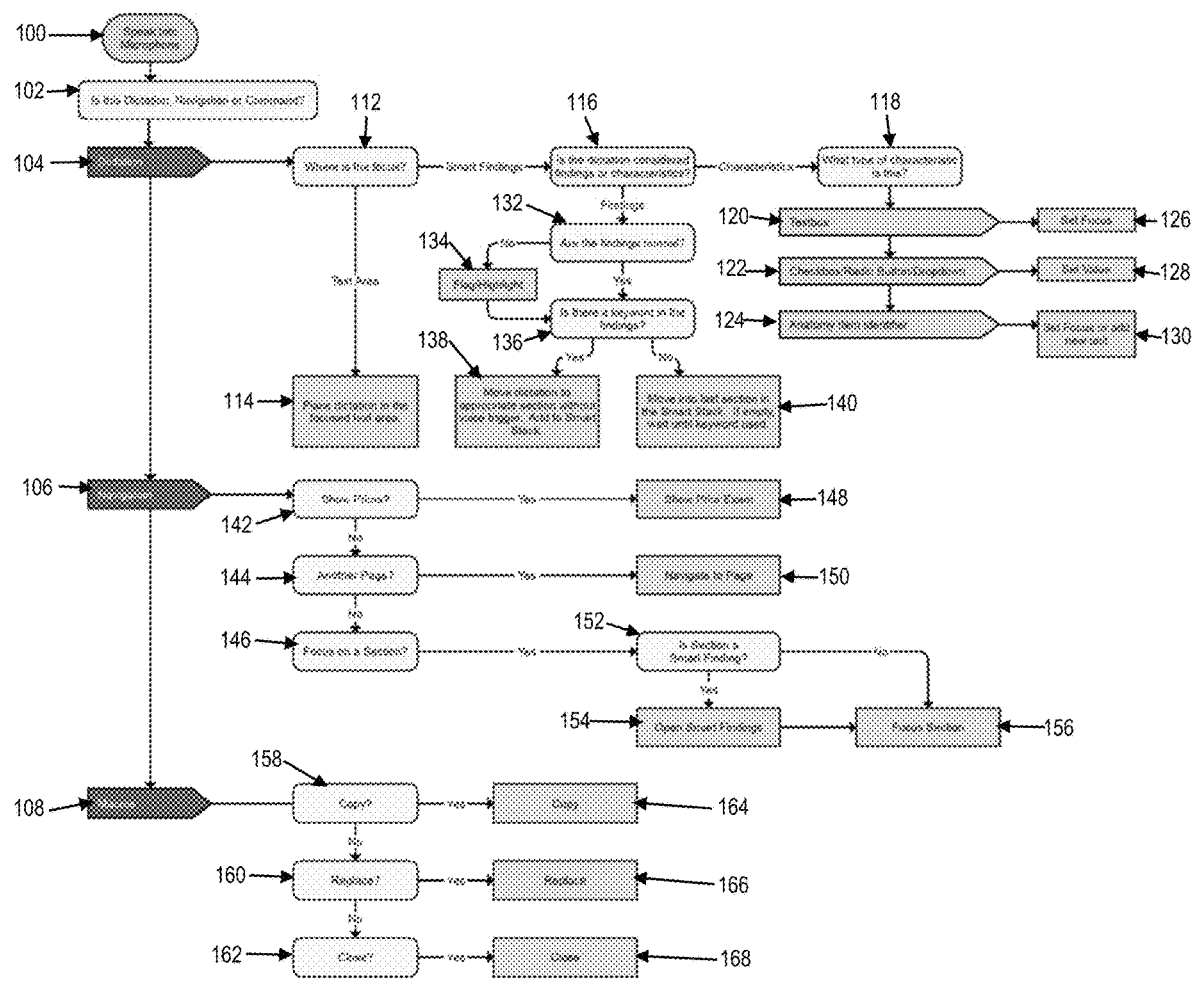
FIG. 4 is a flow chart of an example of a method for generating a voice created clinical structured report.
Figure 7:
FIG. 7 is a screenshot of an example of an initial navigation panel for voice active clinical structured reporting.

An example of a logical structure for clinical structured reporting system 30 is illustrated in FIG. 3. In this example, the clinical structured reporting system 30 includes a smart engine 34 which is coupled to triage raw text and manage algorithms to create executable operations including managing a voice recognition input module 32, a report database 36, a voice executable details logic module 38, a report primer module 40, a raw/processed text module and/or database 42, an internal/external navigation module 44, a macro operations module 46, a template placeholders module 48, and a report module and/or database, although the clinical structured reporting system 30 may comprise other types and/or numbers of modules, databases, programmed instructions and/or other elements in other configurations. As illustrated and described by way of examples herein, the voice input module 32 is used to analyze and triage raw text for the smart engine 34 to identify and manage algorithms to create executable operations for generation of a clinical structured report, although other types of input management modules with other voice processing capabilities may be used. In this example, the report database 36 stores all of the necessary specifications, data, keywords, and default normal and abnormal information to dynamically create any report template from a stored library of pre-defined reports or to obtain from one or more external devices, such as from one of the medical server devices 14(1)-14(n), although the database may store other types and/or amounts of other data and/or may comprise other programmed instructions and/or modules that may be executed to facilitate generation of reports. In this example, the voice executable details logic module 38 processes the raw text to identify one or more words or phrases which the smart engine 34 uses to identify and execute one of a plurality of algorithms to determine one or more executable actions without requiring additional separate explicit voice commands, such as navigation without additional commands to other related sections of the report, and/or retrieval and population of external related data, e.g. imaging data from one of the medical servers 14(1)-14(n) by way of example, although the module may have programmed instructions for other types and/or numbers of operations.

In this example, the report primer module 40 may be implemented based on the identified one or more keywords or phrase by the smart engine 34 and comprises programmed instructions for managing completion of the report and structures for most templates or reports, e.g. fields or regions for patient information, technique, findings, multimedia, impressions, and recommendations, although the module may have programmed instructions for other types of operations and/or other types of data or other content. The report primer module 40 in this example also is configured to be activated by one or more keywords or phrases identified or otherwise detected in the received raw text from the voice audio content input and captured at one of the client devices 16(1)-16(n) that designates the specific report or sub-section of a report requested, such as 'Gall Bladder' report. The report primer module 40 in this example dynamically creates a structured report template placeholder worksheet from the system database or from an external source, such as one of the medical server devices 14(1)-14(n) with a report primer outline structure specific to the report requested based on correlation to the identified one or more keywords or phrases without explicit voice commands making the request. In other examples, the identified one or more keywords or phrases without explicit voice commands can be used by the report primer module 40 to identify requests for multiple organs or anatomical areas with their descriptions to be included in a report as a group. For example, a Complete Abdomen report will have a CPT Code of 76700 (Screen capture, above) requires descriptions of nine organs or specific anatomy. A Limited Abdomen report will have a CPT Code of 75705 and is used for a single organ or any combination of the nine organs/specific anatomy listed in CPT 76700. Uniquely, the user at one of the client devices 16(1)-16(n) can instantly create a large number of specific organ/anatomy combination reports with simple voice inputs converted to raw text and then processed by the voice input module 32 to identified one or more keywords or phrases that the smart engine 34 uses to identify an appropriate one of the algorithms for the smart engine 34 to implement to manage creation of these reports. For example, with the report primer module 40 for the nine organs/anatomy listed in CPT code 75700 a user at one of the client devices 16(1)-16(n) with the identified one or more keywords or phrases has the ability to instantly create the following exemplary organ/anatomy (non-repetitive) combinations of structured clinical reports without mouse/keyboard/microphone tab inputs: for any combination of two organs, 36 reports are instantly available; for any combination of three organs, 84 reports are instantly available; and for any combination of four organs, 126 reports are instantly available. The report primer module 40 also in this example in response to the identified one or more keywords or phrase may trigger navigation of the cursor with navigation module 44 to the requested major sections of the report template, such as patient history, findings, impressions, validation, and the relevant sub-sections of the requested report, without another non-voice input mechanism or explicit separate voice command. Further, the report primer module 40 in this example may dynamically create the report worksheet placeholder template with content which will include the relevant anatomy sections for text or data entry as well as preformatted standard normal default language for each section along with an exam specific relevant library of normal and abnormal macro phrases that may be triggered by the users voice. For example, the requested report code or user's voice may designate a 'Limited Abdomen' Report with the 'Gall Bladder' as the focus of the report. The database will dynamically configure and display a 'Limited Abdomen Gall Bladder' template with default normal language and the relevant library of macro operations specific to the Gall Bladder anatomy In this example, the raw/processed text module and/or database 42 may store and/or manage use of raw/processed text to facilitate generation of the clinical structured report, although the module may store other types of information and/or have programmed instructions for other types of operations. Additionally, in this example, the internal/external navigation module 44 may be implemented based on the identified one or more keywords or phrase by the smart engine 34 to determine and manage navigation within the clinical structured report in, for example, non-linear manners both internally and/or externally to, for example one of the medical server devices 14(1)-14(n) to retrieve necessary data without separate explicit navigation voice commands, although the module may have programmed instructions for other types of operations. In this example, the macro operations module 46 may be implemented based on the identified one or more keywords or phrase by the smart engine 34 and provides programmed instructions to manage one or more macro operations, although the module may have programmed instructions for other types of operations. In this example, the template placeholders module 48 may be implemented based on the identified one or more keywords or phrase by the smart engine 34 and provides programmed instructions to insert and edit report elements, although the module may have programmed instructions for other types of operations. In this example, the report module 50 may be implemented based on the identified one or more keywords or phrase by the smart engine 34 and has programmed instructions to provide the generated clinical structured report to the requesting one of the client devices 14(1)-14(n) or to another designated destination. The completed clinical structured report may, for example, be generated and exported by the report module 50 through, for example, standard host facility IT channels or otherwise export in formats such as PDF, printed form or faxed. Additional aspects and functionality of this example of the logic structure and various modules and databases are illustrated and described in the examples herein.

The communication interface 26 of the voice activated clinical structured reporting device 12 operatively couples and communicates between the voice activated clinical structured reporting device 12, the medical server devices 14(1)-14(n), and/or the client devices 16(1)-16(n), which are all coupled together by the communication networks 18 and 20, although other types and/or numbers of communication networks or systems with other types and/or numbers of connections and/or configurations to other devices and/or elements can also be used.

By way of example only, the communication networks 18 and 20 can include local area network(s) (LAN(s)) or wide area network(s) (WAN(s)), and can use TCP/IP over Ethernet and industry-standard protocols, although other types and/or numbers of protocols and/or communication networks can be used. The communication networks 18 and 20 in this example can employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

The voice activated clinical structured reporting device 12 can be a standalone device or integrated with one or more other devices or apparatuses, such as one or more of the medical server devices 14(1)-14(n), for example. In one particular example, the voice activated clinical structured reporting device 12 can include or be hosted by one of the medical server devices 14(1)-14(n), and other arrangements are also possible.

Each of the medical server devices 14(1)-14(n) in this example includes processor(s), a memory, and a communication interface, which are coupled together by a bus or other communication link, although other numbers and/or types of server and/or network devices could be used. The medical server devices 14(1)-14(n) in this example host medical data and/or other content associated with patient medical records relate to the clinical structured reports, by way of example, although the medical server devices 14(1)-14(n) may host other items of data associated with the processes described herein. The server device 14(1)-14(n) may also host external report elements such as images, video, illustrations, audio, charts, tables and other content as may be required to complete the patient structured report. By way of example only, one or more of the medical server devices 14(1)-14(n) in this example may host applications, such as the EMR (electronic medical record), PACs (Picture Archive and Communication system for image capture), the RIS (Radiology Information Systems for scheduling, order entry, results reporting), and to create templates and content used to create clinical structured reports and other reporting content.

Although the medical server devices 14(1)-14(n) are illustrated as single devices, one or more actions of the medical server devices 14(1)-14(n) may be distributed across one or more distinct network computing devices that together comprise one or more of the medical server devices 14(1)-14(n). Moreover, the medical server devices 14(1)-14(n) are not limited to a particular configuration or to one particular entity and may be managed by multiple different entities. Thus, the medical server devices 14(1)-14(n) may contain a plurality of network devices that operate using a master/slave approach, whereby one of the network devices of the medical server devices 14(1)-14(n) operate to manage and/or otherwise coordinate operations of the other network devices.

The medical server devices 14(1)-14(n) may operate as a plurality of network devices within a cluster architecture, a peer-to peer architecture, virtual machines, or within a cloud architecture, for example. Thus, the technology disclosed herein is not to be construed as being limited to a single environment and other configurations and architectures are also envisaged.

The client devices 16(1)-16(n) in this example include any type of computing device that can interface with the voice activated clinical structured reporting device 12 to submit data and/or receive GUI(s). Each of the client devices 16(1)-16(n) in this example includes a processor, a memory, and a communication interface, which are coupled together by a bus or other communication link, although other numbers and/or types of network devices could be used.

The client devices 16(1)-16(n) may run interface applications, such as standard web browsers or standalone client applications, which may provide an interface to communicate with the voice activated clinical structured reporting device 12 via the communication network(s) 20. The client devices 16(1)-16(n) include a voice interface device, such as a microphone by way of example, to capture voice inputs and may have a speech recognition application to convert the captured voice input to raw text to be provided to the voice activated clinical structured reporting device 12. In this example, the client devices 16(1)-16(n) include a display device, such as a display screen or touchscreen, and one or more other input devices including a microphone or other voice interface device to capture voice input, for example. In one example, the client devices 16(1)-16(n) can be utilized by medical professionals to capture voice inputs and convert to raw text for the intelligent and automated voice activated clinical structured reporting device 12 to use to manage the generation of a clinical structured report as illustrated and described by way of the examples herein.

Although the exemplary network environment 10 with the voice activated clinical structured reporting device 12, medical server devices 14(1)-14(n), client devices 16(1)-16(n), and communication networks 18 and 20 are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the devices depicted in the network environment 10, such as the voice activated clinical structured reporting device 12, client devices 16(1)-16(n), or medical server devices 14(1)-14(n), for example, may be configured to operate as virtual instances on the same physical machine. In other words, one or more of the voice activated clinical structured reporting device 12, client devices 16(1)-16(n), or medical server devices 14(1)-14(n) may operate on the same physical device rather than as separate devices communicating through communication network(s). Additionally, there may be more or fewer voice activated clinical structured reporting devices, client devices, or server devices than illustrated in FIG. 1.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only wireless networks, cellular networks, PDNs, the Internet, intranets, and combinations thereof.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processor(s) to carry out steps necessary to implement the methods of the examples of this technology that are described and illustrated.

An example of a method for generating a voice created clinical structured report with the voice activated clinical structured reporting device 12 will now be illustrated and described with reference to FIGS. 1-14, although in other examples other types of reports could be generated.

First, in these examples to generate a clinical structured report with the voice activated clinical structured reporting device 12 which is managed and provided to one of the client devices 16(1)-16(n), one or more of a plurality of templates or other shell reports or formats needs to be identified and correlated to the patient the user at one of the client devices 16(1)-16(n) is preparing a clinical structured report for. By way of example, selection of an appropriate structured report template and subsections, such as the example illustrated in FIG. 6, may be done by an electronic transmission of an 'order' (request) from one of the client devices 16(1)-16(n) or by an external system (not shown) for a template for an exam type (e.g. Limited Abdomen) and/or and exam code (e.g. 75705) by way of example, or in other examples may be based on a user voice input at one of the client devices 16(1)-16(n), such as a voice input converted to raw text for, 'Limited Abdomen'. Additionally, the patient for whom the clinical structured report is being prepared is typically selected by the user at one of the client devices 16(1)-16(n) from a list of patient names for whom exam or procedure structured reports must be prepared and this selection can be made in a number of different manners, including by voice input converted to raw text, such as starting to speak to prepare the clinical structured report and naming the patient whose background information is then obtained based on natural language processing of the raw text without requiring an explicit voice command for searching for and retrieving the patient information by way of example. In some examples, patient names are added to the list in the form of an 'order' or request by the facility IT system via standard communications protocols from which natural language processing of the raw text without requiring an explicit voice command. An order may by way of example be one or more of the following: exam type, exam code identifier, patient name, medical record number, PACs study identifier, demographic information, age, gender, referring physician, etc. by way of example. The transmitted examination order may be modified or changed by the user at one of the client devices 16(1)-16(n) based on by simply speaking the name of the appropriate examination, 'Kidney', 'Adrenals', 'Chest', etc. thus enabling the smart engine 32 to analyze this natural language without a separate explicit voice command to select one or more structured reporting templates appropriate to the new exam report. Accordingly in the examples herein, this correlation may be based on the identified one or more keywords or phrases from raw text obtained from captured voice input by speech recognition software at one of the user devices 16(1)-16(n) correlated to medical data associated with each of the templates and may be without an explicit voice command for the particular template, although other manners for identifying the template can be used.

Accordingly, before proceeding with the example of a method for generating a voice created clinical structured report with the voice activated clinical structured reporting device 12, an example of one of these templates with the exemplary report template worksheet user interface is illustrated in FIGS. 6-14 and will be described below. In this example, the report template worksheet user interface includes four integrated functional areas of the screen display graphical user interface managed and generated by the voice activated clinical structured reporting device and provided to the requesting one of the client devices 16(1) 16(n). In this example, the four integrated functional areas of the screen display graphical user interface comprise a system navigation toolbar, a left panel, a middle panel, and a right panel as illustrated and described in the examples below, although other types of interfaces with types and/or numbers of other sections in other formats may be used.

In this example, the system navigation toolbar occupies a top-most region of one or more pages of the template and provides report operational functions that may be accessed at any time during the report generation by a user at the requesting one of the client devices 16(1)-16(n). Additionally, in this example this navigation toolbar has the highest z-index and is fixed in its position for all templates and when editing all sections of the template allowing access to its navigation at all times. Further in this example, the navigation toolbar can be further broken down into three exemplary functional panels: a left navigation panel shown in FIG. 7 which includes a primer button E that toggles the report primer view on and off; a middle navigation panel shown in FIG. 8; and a right navigation panel shown in FIG. 9, although other types and/or numbers of navigation panels in other configurations may be used.

Figure 8:
FIG. 8 is a screenshot of an example of an tool bar for voice active clinical structured reporting.

Referring to FIG. 8, the exemplary middle navigation panel has a: home tab that enables navigation to a system home page; patient record tab that navigates the user at one of the client devices 16(1)-16(n) to a patient record page to allow access to other reports; show priors tab that displays a list of selectable prior reports which may be viewed as a pop-up in the current template display and closed on command with only prior exams of same type as the current report being viewed; print tab with other export options for a printable report; a save & sign tab that save all entries in current state and signs the exam as final; email tab that is configured to enable sending the report as email; and reading room tab that toggles day/night mode for report view, although other types and/or numbers of other tabs in other configurations may be used.

Figure 9:
FIG. 9 is a screenshot of an example of another tool bar for voice active clinical structured reporting.

The exemplary right navigation panel shown in FIG. 9 has a: session time indicator tab that allows the user at one of the client devices 16(1)-16(n) to see the time remaining before a session expires and optionally may be turned off at system options level; a username (role) tab that display's the currently logged in user's first name and last name and role (Administrator/Validation/Clerical/custom); and a logout tab that enables the user at one of the client devices 16(1)-16(n) to sign out, although other types and/or numbers of other tabs in other configurations may be used.

As discussed above, the exemplary report template worksheet user interface also includes a left panel, a middle panel, and a right panel, although the template in the interface may other types and/or numbers of other panels. An example of a left panel of a report primer screen for the template is illustrated in FIGS. 6 and 10. In this example for the left panel of the report primer screen, the report primer module 40 with the navigation module 44 includes keywords that enable navigation of active focus of the structured report template for content input based on the identified keywords or phrases by the smart engine 34 without non-voice input mechanisms and without explicit voice navigation operation commands. Accordingly, in these examples the report primer module 40 with the navigation module 44 executed by the voice activated clinical structured reporting device 12 enables the user at one of the client devices 16(1)-16(n) to navigate the active focus of the report template to sections in the template, such as a designated keyword sections within the whole template which otherwise would require use of a separate non-voice input mechanism to move or otherwise scroll to. The user at one of the client devices 16(1)-16(n) may at any time randomly change the active focus for content entry by simply speaking to provide voice input that is converted to raw text received by the voice input module 32 of the voice activated clinical structured reporting device 12 to identify another one or more keywords or phrases that the smart engine 34 can identify as requiring navigation and then may redirect the active focus by implementing the navigation module 44. For example, if the user at one of the client devices 16(1)-16(n) is currently capturing voice input and converting by speech recognition software into raw text that is provided to the voice activated clinical structured reporting device 12 to identify as content to be entered in the report and execute the report primer module 40 to enter into a Liver content section and decides on the fly to enter text comment for the Left Kidney all that is required is for the user at one of the client devices 16(1)-16(n) to say, 'Left Kidney' and the active focus will change (as illustrated with the process above) to the content text box for the Left Kidney. The report primer module 40 also tracks changes in the active focus of the structured report template by highlighting the current active focus keyword for easy user orientation at the one of the client devices 16(1)-16(n). In the screen capture above, the 'Technique' section is highlighted by the voice activated clinical structured reporting device 12 with a purple background indicating to the user at one of the client devices 16(1)-16(n) that the active focus is in the 'Technique' content text box.

In this example, the report primer module 40 in the left panel of the template shown in FIGS. 6 and 10 contains the following navigational keywords, although other numbers and/or types of keywords may be used. Examples of one or more keywords or phrases are listed below:

Exam Information

In this example, these identified keywords or phrases will trigger the smart engine 34 of the voice activated clinical structured reporting device 12 to execute the report primer module 40 to activate either the technologist notes or the examination technique. The technique keyword is highlighted above by the voice activated clinical structured reporting device 12 as the active focus of the structured report section at one of the client devices 16(1)-16(n) and will enable the EDIT mode for, automatic import of the imaging device exam technical specifications, text insertion or editing for the respective section from for example one or more of the medical server devices 14(1)-14(n).

History

In this example, this identified keyword will trigger the smart engine 34 of the voice activated clinical structured reporting device 12 to execute the report primer module 40 to activate a text box and check-box list of exam type specific likely relevant items in the patient's medical history provided the voice activated clinical structured reporting device 12 to the requesting one of the client devices 16(1)-16(n). Voice input converted to raw text and processed by the voice input module 32 to identify one or more keywords or phrase will cause worksheet navigation to the History section of the worksheet by navigation module 44 executed by the voice activated clinical structured reporting device 12 for text insertion and or editing of check-box history items. Mentioning 'edit' before this keyword by the user at one of the client devices 16(1)-16(n) and provided to the voice activated clinical structured reporting device 12 will allow the opening of the section in EDIT mode without any other non-voice input mechanism. Contents of the History section from a prior exam will in this example be automatically be inserted into the current template by the smart engine 34 identifying this content from the one or more keywords or phrase and executing the navigation module 44 invoice activated clinical structured reporting device 12 to retrieve and insert this content, which may be stored externally, such as in one of the medical server devices 14(1)-14(n). In these example, prior check-box elements may be identified by the smart engine 34 based on the identified one or more keywords or phrases may have been stored by the voice activated clinical structured reporting device 12 in a database, such as database 36 and/or 44, as discreet searchable data items with industry standard SQL language that can be retrieved and used to populate a clinical structured report being generated, such as for the same patient. Prior text may also be stored by the voice activated clinical structured reporting device 12 as a 'blob' in the database 36 and/or 44 and may be retrieved and used to populate a clinical structured report being generated, such as for the same patient.

Multimedia

In this example, this identified keyword will activate a horizontal panel or 'band' on the worksheet interface, such as the example of one shown in FIG. 6, for the insertion, editing and manipulation of multimedia elements, such as radiological images, illustrations, charts, videos and other elements obtained for example from one or more of the medical server devices 14(1)-14(n) based on the identified one or more keywords or phrases along with other identifier information, such as patient information by way of example, obtained by smart engine 34 of the voice activated clinical structured reporting device 12 for the one of the client devices 16(1)-16(n) as needed for the report. In this example, mentioning 'edit' as another keyword before this keyword will allow the opening of the section in EDIT mode by the report primer module 40 by the smart engine 34 of the voice activated clinical structured reporting device 12 for the one of the client devices 16(1)-16(n) without the need for another input mechanism.

Summary of Findings

In this example, a Summary of Findings section in the left panel in FIG. 6 reduces large and complex tabular datasets to a few key indicators presented simply in a summary table with only a few data or categorical elements. Additionally, in this example, these identified keywords or phrase will cause the smart engine 34 to identify the report primer module 40 and open one of three or more types of sub-sections for the entry of exam information by the voice activated clinical structured reporting device 12 for the one of the client devices 16(1)-16(n) as needed for the report. In this example, all organ specific sub-sections will also be opened for the one of the client devices 16(1)-16(n) by the report primer module 40 being implemented by the smart engine 34 of the voice activated clinical structured reporting device 12 based on the identified one or more keywords or phrases with default normal statements, although other configurations could be used. If the user at one of the client devices 16(1)-16(n) captures voice input of, 'The Liver appears normal' that is converted to this raw text, then the voice input module 32 will detect the two keywords 'Liver' and 'Normal' and the report primer module 40 implemented based on these one or more keywords or phrase by the smart engine 34 will keep the default normal statement unchanged. If the keyword 'Normal' is not detected in the raw text from the one of the client devices 16(1)-16(n) by the voice input module 32 of the voice activated clinical structured reporting device 12, then the report primer module 40 implemented based on these one or more keywords or phrase by the smart engine 34 will clear the default normal statement and either raw dictation text, processed text, or one or more macro operations will be entered in this example.

In this example, for the exemplary template one or more specific organ sub-sections may open for display at the one of the client devices 16(1)-16(n) by the voice activated clinical structured reporting device 12 for raw or processed text entry depending on the specific exam request processed by the smart engine 34 based on the identified one or more keywords or phrase. Subsequent sub-sections may open automatically for the one of the client devices 16(1)-16(n) by the smart engine 34 of the voice activated clinical structured reporting device 12 based on detection of other subsequently identified one or more keywords or phrase correlated to this operation. For example, if the user at one of the client devices 16(1)-16(n) is entering text into the Liver sub-section and notes that calculi (stones) are present in the Gall Bladder, the smart engine 34 will implement the report primer module 40 executed by the voice activated clinical structured reporting device 12 that will automatically detect 'Gall Bladder' and 'calculi', but not 'Normal' as a keywords and will in this example open an active text box for the Gall Bladder and will activate macro phrases from the macro library specific to a non-normal Gall Bladder, at which time the user at one of the client devices 16(1)-16(n) may provide additional voice input converted to raw text and then analyzed by the input module 32 to identify one or more keywords or phrase to recognize completion of the comments for the Liver and proceed to enter comments with the report primer module 40 for the Gall Bladder without the need for other input mechanisms or other separate explicit voice command to facilitate this action. Alternately, the user at one of the client devices 16(1)-16(n) may provide additional voice input converted to raw text and then analyzed by the input module 32 to identify one or more keywords or phrase that the smart engine 34 of the voice activated clinical structured reporting device 12 determines an indication to choose to complete the entry of comments for the Gall Bladder and initiates the report primer module 40 for this task before returning to complete the Liver comments.

For data intense procedures, such as vascular, tumor size tracking, or serial thyroid surveillance exams, in this example the smart engine 34 of the voice activated clinical structured reporting device 12 based on the identified one or more keywords or phrase may provide a table format from report database 35 for example which is the most efficient mode to organize and display the data. In such cases, a table will automatically open by the smart engine 34 of the voice activated clinical structured reporting device 12 for the one of the client devices 16(1)-16(n) with the appropriate format from database 36 for numerical and categorical (descriptive) data listed in rows and columns based on one or more identified keywords or phrases. In this example, such a table is an efficient way to track interval changes between exams and to calculate indicators such as rate of growth of a tumor, and changes from the baseline exam or prior exam. Numerical measurement data and selected descriptive data may be imported by the navigation module 44 implemented by the smart engine 34 of the voice activated clinical structured reporting device 12 for the table from one of the medical server devices 14(1)-14(n) which has the data for the patient from, for example an imaging device used in a prior examination of the patient. Subsequent calculations upon the imported data may be performed by the voice activated clinical structured reporting device 12 at the database level and displayed in the exam table. Further, additional descriptive data from the identified keywords or phrases may be entered by text or check-box processing by the smart engine 34 implementing the report primer module 40 in the voice activated clinical structured reporting device 12.

Impressions

In this example, the Impressions section in the left panel in FIG. 6 are the diagnostic interpretation of the exam information documented in the structured report template. Impressions entered by way of the voice input captured by the one of the client devices 16(1)-16(n) and converted to raw text and then analyzed by the input module 32 of the voice activated clinical structured reporting device 12 to identify one or more keywords or phrase may be variable based on the clinical interpretation of the report template information. Alternately, Impressions may be pre-defined by professional societies and entered automatically based on categories of findings by the smart engine 34 implementing the report primer module 40 in the voice activated clinical structured reporting device 12 from, for example, one of the medical server devices 14(1)-14(n). Examples of these are the thyroid TI-RADS protocol and the COVID19 protocol as jointly defined by the American College of Radiology (ACR)/Radiological Society of North America (RSNA). In these cases, the voice activated clinical structured reporting device 12 matches the category of findings to the pre-defined diagnosis for the patient and enters it automatically in the Impressions text box.

Recommendations

In this example, a recommendations section in the left panel of FIG. 6 is optional and will, for example, typically suggest a sequential exam, procedure or exam to clarify questions remaining after evaluation of the current information determined based on the obtained data from the raw text from the one of the client devices 16(1)-16(n) and processed by the smart engine 34 of the voice activated clinical structured reporting device 12 and correlated to one or more stored rules or other procedures for recommendations. In other examples, other types and/or numbers of recommendations may be determined in other manners and then may be provided by the voice activated clinical structured reporting device 12.

Validation

In this example, the validation section in the left panel of FIG. 6 is the electronic signature of the certified user of record who is logged into the current template via one of the client devices 16(1)-16(n).

An example of a middle or central panel of a report primer screen for the template is illustrated in FIGS. 6 and 11. In this example, FIGS. 6 and 11 show different examples of sections which may be in the middle or central panel and other configurations may be used. In these examples, the current active worksheet template in this central or middle panel includes sections comprising placeholder fields into which medical examination information content is inserted into the format of a structured report for review, editing, final report generation and export to the one of the client devices 16(1)-16(n) or to other destinations, such as one of the medical server devices 14(1)-14(n) by way of example. Additionally, in this example, the placeholder fields are defined by the template placeholder module 48 implemented by the smart engine 34 based on the identified one or more keywords or phrase and set up by a System Administrator for the types of the clinical structured reports being created. The placeholder fields for the structured report template exist in either an 'active' edit state for the insertion of medical information and editing, or in a 'view' state where the field may not be edited. Executable instructions to determine which state the placeholder fields are in is managed by the smart engine 34 executed by the voice activated clinical structured reporting device 12 responsive to identified keywords or phrase detected by the voice input module 32. For example, a user may say report primer keywords or a phrase, such as "Patient History" to cause the smart engine 34 to implement the report primer module 40 and activate that field for medical information input. Placeholder fields, such as Patient Demographics and Medical Examination information, and Draft Status Notification may be completed by import from internal storage as well as from external systems, such as medical device servers 14(1)-14(n) by way of example. Additionally, placement of medical examination content into the appropriate placeholder field is controlled by the smart engine 34 implementing the report primer module 40 executed by the voice activated clinical structured reporting device 12 in this example. Further, determination of the medical examination specific subject content to retrieve and populate in the report and/or macro operation to implement, are controlled by detection of particular identified keywords or phrase by the smart engine 34 executed by the voice activated clinical structured reporting device 12 in this example.

An example of a right panel of a report primer screen for the template is illustrated in FIGS. 6 and 12. In this example the right panel of the user interface worksheet display shown in the examples in FIGS. 6 and 12 is managed by the smart engine 34 executed by the voice activated clinical structured reporting device 12 based on raw text converted by speech recognition software from voice input captured at one of the client devices 16(1)-16(n). In this illustrative example, four general functional categories of executable instructions may be implemented based on the identified one or more keywords or phrase analyzed by the smart engine 34 of the voice activated clinical structured reporting device 12, although other types and/or numbers of functional categories may be processed. In this example, the user at one of the client devices 16(1)-16(n) may with a voice input converted to raw text that is provided to the voice activated clinical structured reporting device 12: dictate raw text into a text area; trigger a macro function by using a macro keyword; trigger a navigation function by using a navigation keyword; or trigger a functional keyword, although other types and/or numbers of other operations may be used in other examples.

Category 1: Dictation

This section deals with inserting raw text information that would normally be typed by using the keyboard by a user at one of the client devices 16(1)-16(n). In this example, after completion of dictation one of two things in this example may happen: the dictation is not processed, and the text is shown on the screen in the active target text box as dictated; or the text is processed by the voice activated clinical structured reporting device 12, and an appropriate action is taken based on the text. Text processing is done in order to execute instructions for dynamic configuration of the clinical structured report by the report primer module 40 and the template placeholder module 48 by the smart engine based on the identified one or more keywords or phrase, to, for example, determine where text or data elements are to be inserted, to determine which check box to check or uncheck, and other types and/or numbers of related functions for preparing a clinical structured report. The smart engine 34 of the voice activated clinical structured reporting device 12 manages the text algorithms based on identified keywords or phrases to determine executable actions as illustrated and described by way of the examples herein.

Category 2: Macro Keywords—FIG. 13

The user at one of the client devices 16(1)-16(n) captures voice input that is converted by speech recognition software to raw text which is then provided to the voice input module 32 to identify one or more keywords or phrase that triggers the smart engine 34 to implement the report primer module 40 to insert a macro phrase into the targeted text box section or into the Smart Findings Engine text box in the template in this example. An example of how these identified keyword or phrases can trigger executable actions is shown in FIG. 13. These identified keyword or phrases can, for example, be used by the smart engine 32 to initiate the macros module 46 to execute one or more macro operations, such as to copy content of the macro into a section of the report, replace content in the report, or close the report and optionally transmit the report as currently prepared when closed, although other types and/or numbers of macro operations could be identified and executed. In this example, the user at one of the client devices 16(1)-16(n) or another system administrator may define the functionality that is executed with these macro operations by the voice activated clinical structured reporting device 12.

System Defined Macro Keywords—FIG. 14

In this example, exam type specific system defined macro keywords may be stored and activated from the system database library 36 of the voice activated clinical structured reporting device 12 based on one or more identified keywords and phrases. The one or more identified keywords or phrase may simply execute a copy function to enter the macro phrase into the text box, to replace content in the text box or to close the section or report. Certain macro operations executed by the macros module 48 implemented by the smart engine 34 of the voice activated clinical structured reporting device 12 may be set to relate to externally defined reporting protocols, such as the ACR/RSNA TI-RADS and COVID19 reporting guidelines (discussed earlier) where Findings and Impressions are automatically linked by the guideline reporting protocols to control generation of the clinical structured report.

Category 3: Navigation Keywords

The user at one of the client devices 16(1)-16(n) captures voice input that is converted by speech recognition software to raw text which is then provided to the voice input module 32 of to the voice activated clinical structured reporting device 12 that identifies one or more keywords or phrase which are correlated by the smart engine 34 to navigation and cause the navigation module 44 to direct the focus on the screen at one of the client devices 16(1)-16(n) directly to the area of interest without, for example, requiring any scrolling with a mouse or keyboard or other input mechanism or separate explicit voice command. Examples of these identified one or more keywords or phrases correlated by the smart engine 34 by rules and/or stored tables or other information can be further broken down into the following.

Report Navigation Keywords: System defined keywords; Navigate the exam focus to Report Primer report sections: Exam Information, History, Summary of Findings User defined navigation keywords.

The user at one of the client devices 16(1)-16(n) may define custom sections of the report. The section names are treated as navigation keywords which fall under this category. Their functionality is like the system defined navigation keywords the only difference being the user at one of the client devices 16(1)-16(n) is allowed to set them Prior report keywords.

The voice activated clinical structured reporting device 12 allows the user at one of the client devices 16(1)-16(n)

to view a prior report by simply using these keywords or phrase. The format of this group of one or more keywords or phrase is 'Prior Report <Number>'. The smart engine 32 of the voice activated clinical structured reporting device 12 processes the one or more keywords or phrase to determine a which of the number of prior reports to go to, such as a keyword related to identifying each report. The prior report is opened as a pop-up window inside the current window in this example.

Further navigation to a section of the Prior Report is executed by the voice activated clinical structured reporting device 12 by correlating a keyword 'Impressions' or other synonym from a stored database to display the Impressions section of the prior report.

Pop-up window keyword

These keywords or phrase execute an instruction for a pop-up window to appear, setting the focus to another window which may or may not have then functionality.

Page navigation keywords external to the current report template.

Page navigation keywords or phrase navigate away from the current report to either another part of the template, i.e., System Home Page, System Administrator Page, Main Patient Directory Page, Patient Record Page, Patient Exam Directory Page, Patient Demographics Page, Referring Physicians Page, or exiting the system.

Category 4: Functional Keywords

In this example, functional keywords are identified keywords or phrases correlated to executable operations based on rules or other data that do not fall under the prior listed categories. Functional keywords allow the user at one of the client devices 16(1)-16(n) to perform actions on the report that affect the state of report again based on captured voice input converted to raw text by speech recognition software and then processed by the voice input module 32 of voice activated clinical structured reporting device 12 to identify one or more keywords or phrase. Functional keywords may be found throughout the report and are not limited to any section of the report.

When used inside a section, these identified functional keywords enable a user at one of the client devices 16(1)-16(n) to, for example, switch between edit and view mode of the section. In edit mode the user at one of the client devices 16(1)-16(n) may input information into the report. In show mode the user at one of the client devices 16(1)-16(n) may view the section, but may not make changes to it When used in smart findings, these identified functional one or more keywords or phrase allow the user at one of the client devices 16(1)-16(n) to, for example, undo/redo an action, close the smart findings, clear the text inside the smart findings When used in the macro section, these identified one or more functional keywords or phase allow the user at one of the client devices 16(1)-16(n) to close the macro section or switch between different macro sets.

When used in prior reports, these identified one or more functional keywords or phrase navigate to sections of the prior report, such as impressions, prior findings, and prior multimedia.

Accordingly, as illustrated and described by way of example above, the smart engine 32 of the voice activated clinical structured reporting device 12 based on the identified one or more keywords or phrase along with other data or current status information, such as a combination of the identified one or more keywords or phrase along with a current particular section or band being generated in the clinical structured report, the smart engine 32 is able to analyze and determine which algorithm(s) initiate along with what particular functionality or functionalities to execute. The smart engine 32 may also comprise artificial intelligence which is trained based on the generation of prior clinical structured reports in different contexts along with corrective feedback to implement the generation of this report automatically without other input mechanisms and in some examples without additional explicit voice commands for particular operations.

Referring now more specifically to FIG. 3, in step 100 by the voice activated clinical structured reporting device 12 receives a captured voice input converted to raw text related to generating a clinical structured report from one of the client devices 16(1)-16(n), although the voice audio content could be received from other sources. For example, the captured voice input in other examples could be converted to raw text at other locations, such as with the voice activated clinical structured reporting device 12. In this example, the voice input module 32 of the voice activated clinical structured reporting device 12 applies one or more natural language processing algorithms to the raw text from the one of the client devices 16(1)-16(n) to identify one or more keywords or phrases, although other manners for identifying one or more keywords or phrases can be used. The voice activated clinical structured reporting device 12 may also correlate the identified one or more keywords or phrases to one of a plurality of stored templates or other reports with one or more fields or other section to customize from, for example, report database 38 and/or externally, such as from one of the medical server devices 14(1)-14(n), although other manners for identifying and obtaining a template or report to complete may be used. The voice activated clinical structured reporting device 12 may also obtain information about the patient the template or report is being prepared for from other voice audio content provided at the start and/or obtained from one of the medical server devices 14(1)-14(n) by way of example, although other manners for gathering this information may be used. The voice activated clinical structured reporting device 12 may, for example, execute the navigation module 44 to identify and obtain this content.

In step 102, in this example the smart engine 34 of the voice activated clinical structured reporting device 12 determines based on one or more stored rules whether the identified one or more keywords or phrases and/or other information, such as in what section or band the last report generation operation was executed, correlate to functionality, such as dictation, navigation, or a macro, although the correlation could be to other types and/or numbers of executable actions or other functionality to manage generation of a clinical structured report. By way of example only, the stored rules may recognize a pattern in the identified one or more keywords or phrases consistent with dictation, may recognize one or more navigation actions are needed based on a correlation of the identified one or more keywords or phrases to different related sections of a template that need to be filled and/or modified, and/or may recognize that the identified one or more keywords or phrases correlate to one or more macro operations for an executable action related to the current version of the clinical structured report, although other manners for determining executable actions from the identified one or more keywords or phrases without any other input mechanisms including additional explicit voice commands specifying the executable actions. Accordingly, the claimed technology is able to identify and execute these additional executable actions more quickly and seamlessly.

If in step 102, the smart engine 34 of the voice activated clinical structured reporting device 12 determines the identified one or more keywords or phrases correlate to dictation, then the voice activated clinical structured reporting device 12 proceeds to begin to manage dictation in step 104. Next, in step 112, the voice activated clinical structured reporting device 12 determines whether a focus of the identified one or more keywords or phrases is directed to a smart finding, as illustrated for example in FIG. 12, or a text area, although other types and/or numbers of focus areas may be used. If in step 112 the voice activated clinical structured reporting device 12 determines the focus is directed to a text area, then in step 114 the voice activated clinical structured reporting device 12 may place the raw text associated with the identified one or more keywords or phrases as dictation in a correlated one of the fields in the template or report being prepared.

If back in step 112 the voice activated clinical structured reporting device 12 determines the focus is directed to a smart finding, then in step 116 the voice activated clinical structured reporting device 12 determine whether the one or more keywords or phrases identified as dictation relate to findings or characteristics, although correlations to other types of executable actions may be used. If in step 116 the voice activated clinical structured reporting device 12 determine the one or more keywords or phrases identified as dictation are related to characteristics, then in step 118 the voice activated clinical structured reporting device 12 determines whether the one or more keywords or phrases identified as dictation are related to: a textbox; a checkbox/radio button/dropdown; or an anatomy item identifier, although identifications to other types of elements could be used.

If in step 118, the voice activated clinical structured reporting device 12 determines the one or more keywords or phrases identified as dictation are related to a textbox in step 120, then in step 126 the voice activated clinical structured reporting device 12 can set a focus on an identified one of the textboxes in the template or report and then may return to step 100

If back in step 118, the voice activated clinical structured reporting device 12 determines the one or more keywords or phrases identified as dictation are related to a checkbox/radio button/dropdown in step 122, then in step 128 the voice activated clinical structured reporting device 12 can set a value in the identified one of the checkbox/radio button/dropdown in the template or report based on the identified one or more keywords or phrases and then may return to step 100.

If back in step 118, the voice activated clinical structured reporting device 12 determines the one or more keywords or phrases identified as dictation are related to an anatomy item identifier in step 124, then in step 130 the voice activated clinical structured reporting device 12 can set a focus or add a new unit in the template or report based on the identified one or more keywords or phrases and then may return to step 100.

If back in step 116 the voice activated clinical structured reporting device 12 determine the one or more keywords or phrases identified as dictation are related to findings, then in step 132 the voice activated clinical structured reporting device 12 may use the smart engine 34 obtain other related stored data from an internal storage device and/or obtain data from one or more of the medical server devices 14(1)-14(n) with execution of the navigation module 44 to analyze and determine if the findings in the raw text are normal, e.g. above or below thresholds and/or within ranges for the finding. If in step 132 the voice activated clinical structured reporting device 12 determines the findings are not normal, then the No branch is taken to step 134 where the findings are noted in the template or report and flagged or otherwise identified as not normal, flagged or highlighted by way of example. If in step 132 the voice activated clinical structured reporting device 12 determines the findings are normal, then the Yes branch is taken to step 136 to where dictation is moved to the correct location in a section of the report to populate as needed for a normal.

If in step 136 the voice activated clinical structured reporting device 12 determines there is one keyword correlated to the current area of focus in a section or band of the template, such as by a comparison of the identified one or more keywords or phrases against particular stored keywords for the section or band by way of example only, then the Yes branch is taken to step 138 where the dictation comprising the raw text is placed in a correlated field or other appropriate section or band of the template or report by the voice activated clinical structured reporting device 12 without any additional voice trigger or other input mechanism and then may return to step 100. If back in step 136 the voice activated clinical structured reporting device 12 determines there is not one keyword correlated to any part of the current template, then the No branch is taken to step 140 where the dictation comprising the one or more identified keywords or phrases is placed into a smart stack or other storage location for possible correlation and later use or to be discarded if not needed and then may return to step 100.

If back in step 102, the voice activated clinical structured reporting device 12 determines the identified one or more keywords or phrases correlate to navigation, then the voice activated clinical structured reporting device 12 proceeds to begin to manage navigation in step 106. Next, in step 142 the voice activated clinical structured reporting device 12 determines from a previously trained intelligent analysis of correlation of navigation options to one or more identified keywords or phrases, whether the identified one or more keywords or phrases correlate to navigation options to: show priors; another page; or focus on a section in this example, although other types and/or numbers of other navigation options could be used and other manners for determining the navigation options could be used.

If in step 142 the voice activated clinical structured reporting device 12 determines the identified one or more keywords or phrases correlate to a navigation option to show priors in step 142, then in step 148 the voice activated clinical structured reporting device 12 retrieves a prior examination or report with the navigation module 44 from internal storage and/or from one or more of the medical server devices 14(1)-14(n) in this example based on the identified one or more keywords or phrase by the smart engine 32 and provides them for display at the requesting one of the client devices 16(1)-16(n) until receipt of other voice content and then may return to step 100, although other types of prior content could be provided based on the patient and report being generated.

If back in step 142 the voice activated clinical structured reporting device 12 determines the identified one or more keywords or phrases correlate to a navigation option to go to another page in step 144, then in step 150 the smart engine 32 implements the navigation module 44 in the voice activated clinical structured reporting device 12 to navigate to another page of the template or report being generated correlated to the identified one or more keywords or phrases, such as another page with fields correlated to the identified one or more keywords or phrases until receipt of other voice content and then may return to step 100.

If back in step 142 the voice activated clinical structured reporting device 12 determines the identified one or more keywords or phrases correlate to a navigation option to focus on a section in step 146, then in step 152 the smart engine 32 of the voice activated clinical structured reporting device 12 determines whether the determined section is a smart finding based on at least the identified one or more keywords or phrase, although other content in the raw text and/or other related contextual information based on current status may be used by way of example. If in step 152 the voice activated clinical structured reporting device 12 determines the section is not a smart finding, then the No branch is taken to step 156 where the focus provided to the requesting one of the client devices 16(1)-16(n) is on the section. If in step 152 the voice activated clinical structured reporting device 12 determines the section is a smart finding, such as a current determined analysis and/or stage of a condition or other medical determination or status by way of example, then the Yes branch is taken to step 154 where the smart findings are opened and then in step 156 the focus for the requesting one of the client devices 16(1)-16(n) is on the smart finding in the section until receipt of other voice content and then may return to step 100.

If back in step 102, the smart engine 34 of the voice activated clinical structured reporting device 12 determines the identified one or more keywords or phrases correlate to one of a plurality of macro operations, then the voice activated clinical structured reporting device 12 proceeds to step 108 to determine if the macro is: copy; replace; or close in this example, although other types and/or numbers of macro operations could be used.

If in step 108 the voice activated clinical structured reporting device 12 determines the identified one or more keywords or phrases correlate to the macro copy in step 158, then in step 164 the voice activated clinical structured reporting device 12 executes a copy macro to copy content into the template or report and then may return to step 100. If back in step 108 the voice activated clinical structured reporting device 12 determines the identified one or more keywords or phrases correlate to the macro replace in step 160, then in step 166 the voice activated clinical structured reporting device 12 executes a replace macro to replace content into the template or report and then may return to step 100. If back in step 108 the voice activated clinical structured reporting device 12 determines the identified one or more keywords or phrases correlate to the macro close in step 162, then in step 168 the voice activated clinical structured reporting device 12 executes a close macro to close a section or the template or report and then may return to step 100.

When the voice activated clinical structured reporting device 12 determines the clinical structured report is completed and/or receives or identifies any other indication that generation of the report has reached a particular stage, then the generated clinical structured report may be provided in a number of manners to the requesting one of the client devices 16(1)-16(n) and/or other destinations, such as in a stored patient record in one of the medical server devices 14(1)-14(n) and/or to a designated physician's computing device. An example of a screenshot a user display of an exemplary clinical structured report generated with one of these templates and provided to the requesting one of the client devices 16(1)-16(n) and/or other destinations is shown in FIG. 5.

Accordingly, as illustrated and described by way of the examples herein, this technology provides a number of advantages including providing an intelligent automated voice activated clinical reporting system that eliminates the need for separate mouse, keyboard, and microphone and 'tab+command' systems and, in some examples, without additional separate explicit voice commands as input mechanisms to accurately generate clinical structured reports. Examples of this technology address at least three major issues characteristic of contemporary structured reporting template systems as discussed above including: (1) hardware limitations; (2) navigation limitations; and (3) lack of intelligence of the system. These prior issues have historically affected the accuracy, ease of report preparation, speed of generation of a clinical report, and importantly a user's productivity which examples of the claimed technology are able to overcome. By way of example, this technology manages a "smart engine" of intelligent algorithms which detect keywords and phrases in natural language speech as inputs which automatically create instructions for executable processes to create examination specific report templates, select and manipulate multimedia report elements, and enable automatic and dynamic template and system navigation processes, without additional explicit voice commands, for the generation of a completed clinical structured patient report. Examples of this technology utilize voice activated executable algorithms managed by a smart engine to navigate the active focus within and/or external to the structured report template to select, insert, accept, and manipulate text and multimedia report elements necessary for report generation. Accordingly, examples of this technology have adapted integrated speech recognition without additional and separate explicit voice commands as the sole input component to manage an integrated system of intelligent algorithms responsive to automatically create instructions for executable processes to generate a completed clinical structured report. As a result, with this technology, a user is able to focus on critical diagnostic implications of the findings of the clinical or procedure at hand and is freed from the distraction and clumsiness of separate mouse, keyboard, and microphone and 'tab+command' systems as input mechanisms or even the requirement for additional explicit voice commands.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method of automatically generating clinical structured reports based on clinical structured report templates using voice recognition, the method implemented by one or more report management computing devices and comprising:

identifying one or more key words or phrases in a voice input comprising natural language speech;

identifying at least one clinical structured report template associated with medical data comprising medical examination data points based on the identified one or more key words or phrases;

determining an action category for the one or more key words or phrases in the voice input, wherein the action category comprises navigation that comprises a navigation action that navigates active focus external to the clinical structured report without a separate explicit voice command for the navigation externally;

automatically generating a clinical structured report based on the clinical structured report template, wherein the generated clinical structured report includes modifications to the clinical structured report template based on the identified one or more key words or phrases; and generating and outputting executable instructions for graphical user interface display of the clinical structured report.

2. The method of claim 1,
wherein the action category further comprises one or more of dictation or macros, wherein the modifications to the clinical structured report are based on the determined action category.

3. The method of claim 2, wherein the determined action category is dictation, the method further comprising:
identifying a focus area of the one or more key words or phrases, wherein the focus area comprises one of a text area of the clinical structured data report or a smart finding associated with the medical examination points; and
modifying the clinical structured report based on the identified focus area.

4. The method of claim 3, wherein the identified focus area is a text area, the method further comprising:
placing the one or more key words or phrases in the text area of the clinical structured data report.

5. The method of claim 3, wherein the identified focus area is a smart finding associated with the medical examination points, the method further comprising:
determining a finding category of the smart finding, wherein the finding category comprises one or more of a medical finding or a characteristic.

6. The method of claim 5, wherein the finding category is a medical finding, the method further comprising:
determining whether the medical finding comprises an abnormal finding; and
modifying the clinical report to identify the abnormal finding when the medical finding comprises the abnormal finding.

7. The method of claim 5, wherein the finding category is a medical finding, the method further comprising:
determining whether the medical finding comprises an identifying keyword; and
inserting the medical finding into the clinical structured report based on the identifying keyword.

8. The method of claim 5, wherein the finding category is a characteristic, the method further comprising:
determining a characteristic type of the characteristic, wherein the characteristic type comprises one of an anatomy item, a text item, or a display item; and
adjusting the clinical structured report based on the determined characteristic type.

9. The method of claim 2, wherein the determined category is the navigation, the method further comprising:

determining another navigation action within the clinical structured report based on the one or more keywords; and
outputting executable instructions to adjust the graphical user interface display of the clinical structured report based on the another navigation action.

10. The method of claim 9, wherein the another navigation action comprises focusing on a section of the clinical structured report.

11. The method of claim 10, wherein the another navigation action comprises the focusing on a section of the clinical structured report, the method further comprising:
determining whether the focusing relates to a smart finding associated with the medical examination points; and
outputting executable instructions to adjust the graphical user interface display of the clinical structured report to open the smart finding when the focusing relates to the smart finding.

12. The method of claim 2, wherein the determined action category is macros, wherein the method further comprises:
identifying one or more macros based on the one or more keywords;
modifying the clinical structured report based on the identified one or more macros.

13. A voice activated clinical structured reporting device, comprising memory comprising programmed instructions stored thereon and one or more processors configured to execute the stored programmed instructions to:
identifying one or more key words or phrases in a voice input comprising natural language speech;
identify at least one clinical structured report template associated with medical data comprising medical examination data points based on the identified one or more key words or phrases;
determine an action category for the one or more key words or phrases in the voice input, wherein the action category comprises navigation that comprises a navigation action that navigates active focus external to the clinical structured report without a separate explicit voice command for the navigation externally;
automatically generate a clinical structured report based on the clinical structured report template, wherein the generated clinical structured report includes modifications to the clinical structured report template based on the identified one or more key words or phrases; and
generate and output executable instructions for graphical user interface display of the clinical structured report.

14. The device of claim 13,
wherein the action category further comprises one or more of dictation, or macros, wherein the modifications to the clinical structured report are based on the determined action category.

15. The device of claim 14, wherein the determined action category is dictation, wherein the processors are further configured to execute the stored programmed instructions:
identify a focus area of the one or more key words or phrases, wherein the focus area comprises one of a text area of the clinical structured data report or a smart finding associated with the medical examination points; and
modify the clinical structured report based on the identified focus area.

16. The device of claim 15, wherein the identified focus area is a text area, wherein the processors are further configured to execute the stored programmed instructions to:

place the one or more key words or phrases in the text area of the clinical structured data report.

17. The device of claim 15, wherein the identified focus area is a smart finding associated with the medical examination points, wherein the processors are further configured to execute the stored programmed instructions to:
determine a finding category of the smart finding, wherein the finding category comprises one or more of a medical finding or a characteristic.

18. The device of claim 17, wherein the finding category is a medical finding, wherein the processors are further configured to execute the stored programmed instructions to:
determine whether the medical finding comprises an abnormal finding; and
modify the clinical report to identify the abnormal finding when the medical finding comprises the abnormal finding.

19. The device of claim 17, wherein the finding category is a medical finding, wherein the processors are further configured to execute the stored programmed instructions to:
determine whether the medical finding comprises an identifying keyword; and
insert the medical finding into the clinical structured report based on the identifying keyword.

20. The device of claim 17, wherein the finding category is a characteristic, wherein the processors are further configured to execute the stored programmed instructions to:
determine a characteristic type of the characteristic, wherein the characteristic type comprises one of an anatomy item, a text item, or a display item; and
adjust the clinical structured report based on the determined characteristic type.

21. The device of claim 14, wherein the determined category is the navigation, wherein the processors are further configured to execute the stored programmed instructions to:
determine another navigation action within the clinical structured report based on the one or more keywords; and
output executable instructions to adjust the graphical user interface display of the clinical structured report based on the another navigation action.

22. The device of claim 21, wherein the another navigation action comprises focusing on a section of the clinical structured report.

23. The device of claim 22, wherein the another navigation action comprises the focusing on a section of the clinical structured report, wherein the processors are further configured to execute the stored programmed instructions to rising:
determine whether the focusing relates to a smart finding associated with the medical examination points; and
output executable instructions to adjust the graphical user interface display of the clinical structured report to open the smart finding when the focusing relates to the smart finding.

24. The device of claim 14, wherein the determined action category is macros, wherein the processors are further configured to execute the stored programmed instructions to:
identify one or more macros based on the one or more keywords;
modify the clinical structured report based on the identified one or more macros.

25. A non-transitory machine readable medium having stored thereon instructions for voice activate clinical structured reporting comprising executable code that, when executed by one or more processors, causes the processors to:
identify one or more key words or phrases in a voice input comprising natural language speech;
identify at least one clinical structured report template associated with medical data comprising medical examination data points based on the identified one or more key words or phrases;
determine an action category for the one or more key words or phrases in the voice input, wherein the action category comprises navigation that comprises a navigation action that navigates active focus external to the clinical structured report without a separate explicit voice command for the navigation externally;
automatically generate a clinical structured report based on the clinical structured report template, wherein the generated clinical structured report includes modifications to the clinical structured report template based on the identified one or more key words or phrases; and
generate and output executable instructions for graphical user interface display of the clinical structured report.

26. The medium of claim 25,
wherein the action category further comprises one or more of dictation or macros, wherein the modifications to the clinical structured report are based on the determined action category.

27. The medium of claim 26, wherein the determined action category is dictation, wherein the executable code, when executed by the processors, further causes the processors to:
identify a focus area of the one or more key words or phrases, wherein the focus area comprises one of a text area of the clinical structured data report or a smart finding associated with the medical examination points; and
modify the clinical structured report based on the identified focus area.

28. The medium of claim 27, wherein the identified focus area is a text area, wherein the executable code, when executed by the processors, further causes the processors to:
place the one or more key words or phrases in the text area of the clinical structured data report.

29. The medium of claim 27, wherein the identified focus area is a smart finding associated with the medical examination points, wherein the executable code, when executed by the processors, further causes the processors to:
determine a finding category of the smart finding, wherein the finding category comprises one or more of a medical finding or a characteristic.

30. The medium of claim 29, wherein the finding category is a medical finding, wherein the executable code, when executed by the processors, further causes the processors to:
determine whether the medical finding comprises an abnormal finding; and
modify the clinical report to identify the abnormal finding when the medical finding comprises the abnormal finding.

31. The medium of claim 29, wherein the finding category is a medical finding, wherein the executable code, when executed by the processors, further causes the processors to:
determine whether the medical finding comprises an identifying keyword; and
insert the medical finding into the clinical structured report based on the identifying keyword.

32. The medium of claim 29, wherein the finding category is a characteristic, wherein the executable code, when executed by the processors, further causes the processors to:

determine a characteristic type of the characteristic, wherein the characteristic type comprises one of an anatomy item, a text item, or a display item; and adjust the clinical structured report based on the determined characteristic type.

33. The medium of claim 26, wherein the determined category is the navigation, wherein the executable code, when executed by the processors, further causes the processors to:

determine the another navigation action for the clinical structured report based on the one or more keywords; and output executable instructions to adjust the graphical user interface display of the clinical structured report based on the another navigation action.

34. The medium of claim 33, wherein the another navigation action comprises focusing on a section of the clinical structured report.

35. The medium of claim 34, wherein the another navigation action comprises the focusing on a section of the clinical structured report, wherein the executable code, when executed by the processors, further causes the processors to:

determine whether the focusing relates to a smart finding associated with the medical examination points; and output executable instructions to adjust the graphical user interface display of the clinical structured report to open the smart finding when the focusing relates to the smart finding.

36. The medium of claim 26, wherein the determined action category is macros, wherein the executable code, when executed by the processors, further causes the processors to:

identify one or more macros based on the one or more keywords;

modify the clinical structured report based on the identified one or more macros.

* * * * *